United States Patent
Furukawa et al.

(10) Patent No.: US 6,997,952 B2
(45) Date of Patent: Feb. 14, 2006

(54) ARTIFICIAL SPHINCTER

(75) Inventors: Akihisa Furukawa, Sendai (JP); Toshiyuki Takagi, Sendai (JP); Hidetoshi Matsuki, Sendai (JP); Yun Luo, 68-6-44, Kawauchikameokacho, Aoba-ku, Sendai-shi, Miyagi (JP); Junko Hayashi, Sendai (JP); Tomoyuki Yambe, Sendai (JP); Takamichi Kamiyama, Sendai (JP); Shintaro Amae, Sendai (JP); Motoshi Wada, Sendai (JP)

(73) Assignees: NEC Tokin Corporation, Miyagi (JP); Toshiyuki Tagaki, (JP); Yun Luo, Miyagi (JP)

( * ) Notice: Subject to any disclaimer, the term of this patent is extended or adjusted under 35 U.S.C. 154(b) by 0 days.

(21) Appl. No.: 10/889,154

(22) Filed: Jul. 12, 2004

(65) Prior Publication Data

US 2004/0243236 A1 Dec. 2, 2004

Related U.S. Application Data

(62) Division of application No. 09/866,448, filed on May 25, 2001, now Pat. No. 6,830,588.

(30) Foreign Application Priority Data

Mar. 8, 2001 (JP) ............................. 2001-65197

(51) Int. Cl.
  *A61F 2/08* (2006.01)

(52) U.S. Cl. .................. 623/14.13; 600/30; 600/23.64; 600/24

(58) Field of Classification Search ............. 623/11.11, 623/14.13, 23.64–23.67, 23.71, 24; 600/29, 600/30

See application file for complete search history.

(56) References Cited

U.S. PATENT DOCUMENTS

| | | | |
|---|---|---|---|
| 3,247,476 A | * | 4/1966 | Pintell .................... 336/177 |
| 3,522,811 A | * | 8/1970 | Wingrove et al. ......... 607/27 |
| 4,556,050 A | * | 12/1985 | Hodgson et al. .......... 600/30 |
| 5,008,649 A | * | 4/1991 | Klein ................... 340/572.3 |
| 6,162,238 A | * | 12/2000 | Kaplan et al. ........... 606/201 |

* cited by examiner

*Primary Examiner*—Corrine McDermott
*Assistant Examiner*—William H Matthews
(74) *Attorney, Agent, or Firm*—Bradley N. Ruben

(57) ABSTRACT

With an object of providing an artificial sphincter for which repeated shape changes are possible, and for which the quantity of shape change is sufficient so as to be used as a substitute for a large natural sphincter, an artificial sphincter 11 that opens and closes, as required, either the anus of a living body or part of the intestine 19 led outside the body is provided, wherein this artificial sphincter 11 comprises a pair of shape memory alloy elements 13 that change reversibly between two opposite shapes upon changes in temperature and hinges 15 that link the shape memory alloy elements 1 together in a cylindrical shape.

12 Claims, 5 Drawing Sheets

ARTIFICIAL SPHINCTER

CROSS REFERENCE TO RELATED APPLICATIONS

This application is a division of U.S. patent application Ser. No. 09/866,448 filed May 25, 2001, now U.S. Pat. No. 6,830,588.

BACKGROUND OF THE INVENTION

1. Field of the Invention

The present invention relates to an artificial sphincter used, for example, when the anal sphincter has been removed or when there has been a decline in the functioning of a sphincter.

2. Description of the Related Art

Conventionally, in cases such as when development of the anal sphincter is incomplete due to infantile rectal/anal malformation or when the anal sphincter is removed due to colonic cancer as an adult, an artificial anus is used.

An artificial anus commonly used conventionally is formed by sewing the intestine so as to open out at the surface of the body, and then attaching a pouch to the surface of the body so as to cover this intestinal opening.

With all pouches available on the market, the whole or part of the pouch must be replaced after defecation, and an unpleasant odor may leak out. Due to such problems, there is a drawback that everyday social life becomes troublesome.

There are artificial anuses having a stopper for which pouch replacement is not necessary. With these artificial anuses, a T-shaped cover is set into a flange that covers the aforementioned intestinal opening. There is an inconvenience in that, every time defecation occurs, the cover must be removed and then reattached. Moreover, there is also the possibility of excrement or gas leaking out from gaps between the cover and the opening.

To resolve the drawbacks of the pouch method, an artificial anus has been proposed in which an intestine opening/closing portion comprising a shape memory alloy is provided around an intestinal opening in the body, and the intestinal opening on the surface of the body is heated by passing a current from a battery embedded in the body, thus changing the shape of the shape memory alloy and opening/closing the intestinal opening (Japanese Patent Application Laid-open No. H4-319349; hereinafter referred to as 'Prior Art Document 1').

With the artificial anus of Prior Art Document 1, the scope of activity of the patient is widened, with no removal or replacement being necessary after defecation, and moreover because a shape memory alloy is used, a sufficient constricting force can be generated, resulting in excrement leakage and unpleasant odors being prevented.

With an artificial anus such as that disclosed in Prior Art Document 1, in which an intestine opening/closing portion comprising a shape memory alloy is provided around an intestinal opening in the body, and the intestinal opening on the surface of the body is heated by passing a current from a battery embedded in the body, thus changing the shape of the shape memory alloy and opening/closing the intestinal opening, a ring-shaped shape memory alloy element is used, and the structure is such that the intestinal opening is closed when the shape memory alloy is squashed flat. The power source for heating is covered in a case of a material having good affinity with living bodies, such as a polysulfone, and a small battery and a push switch are provided inside.

In this way, heating is carried out by passing a current from the small battery embedded in the body, thus changing the shape of the shape memory alloy and opening/closing the intestinal opening.

However, the shape memory alloy (SMA) ring used here has locally large distortion and poor repetition characteristics, making it difficult to change the shape repeatedly. Moreover, when a shape memory alloy element is embedded in a narrow region, namely an intestinal opening on the surface of the body, the intestine is subjected to a local force, and there is thus a risk of damage to this part of the body.

Moreover, the power source for heating is embedded between the skin and the muscularis, meaning that replacement when the small battery has been exhausted is troublesome. In particular, the small battery and the push switch that constitute the power source for heating are connected to the shape memory alloy (SMA) ring via a lead wire, and so the choice of installment location is somewhat limited.

Furthermore, the lead wire must be a certain length, and there is a risk of infection along this part.

One could also envisage transmitting electrical power into the body from a power source outside the body via a lead wire, but then there would be a risk of infection from the electrode part passing through to the outside of the body.

Moreover, even in the case of a 2-way shape memory alloy, it is difficult to achieve a quantity of shape change from the state in which the ring is squashed flat such that the opening opens to a sufficient size for unimpeded defecation to be possible.

SUMMARY OF THE INVENTION

It is an object of the present invention to provide an artificial sphincter for which repeated shape changes are possible, and for which the quantity of shape change is sufficient so as to be used as a substitute for a natural sphincter.

It is another object of the present invention to provide an artificial sphincter that eliminates inconveniences of the aforementioned conventional examples, and for which electrical power supply is possible without passing a lead wire through the skin, thus avoiding risk of infection.

According to one aspect of the present invention, there is provided an artificial sphincter having an opening/closing portion for opening and closing is obtained, wherein the opening/closing portion has a pair of elongated memory alloy elements that change reversibly between opposite shapes upon changes in temperature.

Moreover, according to another aspect of the present invention, there is provided an artificial sphincter comprising a shape memory alloy opening/closing portion and temperature controlling heaters is obtained, wherein electrical power is supplied to the temperature controlling heaters by a percutaneous electrical power transmission system having a coil on the side connected to the power source as a primary coil and a coil on the side connected to the load as a secondary coil. The electrical power may be supplied without using a lead wire.

DESCRIPTION OF THE PREFERRED EMBODIMENTS

Description will be made as regards the preferred embodiment according to the present invention with reference to FIG. 1–10.

(First Embodiment)

Figure 1:
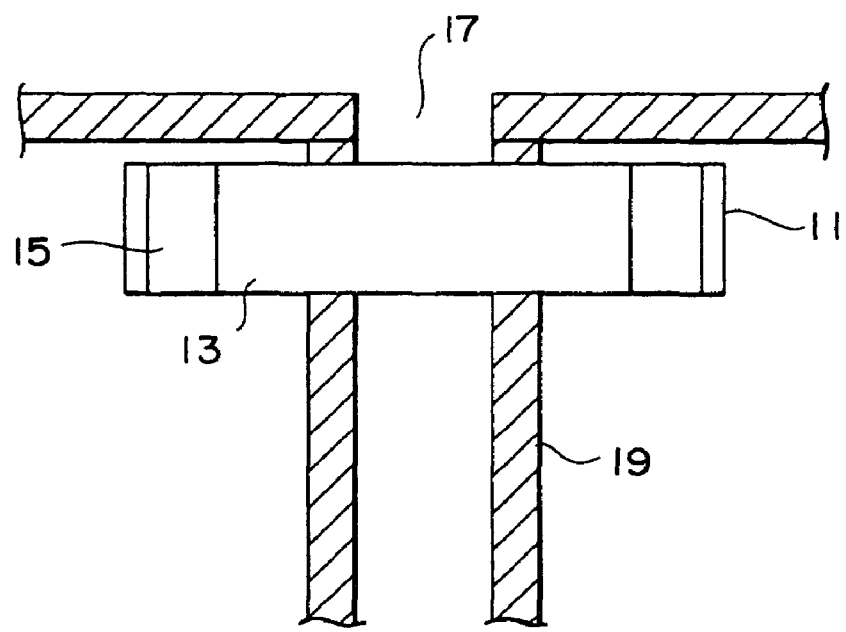
FIG. 1 is a schematic drawing showing the principal parts of an artificial sphincter according to a first embodiment of the present invention.

As shown in FIG. 1, an opening/closing portion 11 of an artificial sphincter according to a first embodiment comprises a pair of plate-like shape memory alloy elements (hereinafter referred to as 'shape memory plates') 13 each having a 2-way shape memory property, and hinges 15 provided so as to join together end parts of the shape memory plates 13. The opening/closing portion 11 is attached around the intestine 19 of a human or animal inside the body near to an intestinal opening 17.

For the opening/closing portion 11 of the artificial sphincter, Ti—Ni alloy plates (Ni content 50.4 at %) of thickness 0.8 mm, length 100 mm and width 20 mm are given a 2-way shape memory property. The 2-way shape memory property is obtained by subjecting the plates to solution heat treatment at 700° C. for 30 minutes, and then, while restrained at a curvature of R40 mm, to aging heat treatment at 400° C. for 100 hours. If heated to 40° C., these plates return to the shape at the time of the aging heat treatment at 400° C. for 100 hours. If cooled to body temperature, the plates change shape, bending backwards in the opposite direction. In each case, the curvature is about R40 mm.

Two 2-way shape memory plates 13 prepared in this way are used, and these 2-way shape memory plates 13 are linked to the intestine 19 near to the intestinal opening in a cylindrical shape using the hinges 15 in such a way that the inside of each of the 2-way shape memory plates 13 is in the direction of the restraining that was carried out during the aging heat treatment, thus forming the opening/closing portion 11 of the artificial sphincter.

Figure 2:
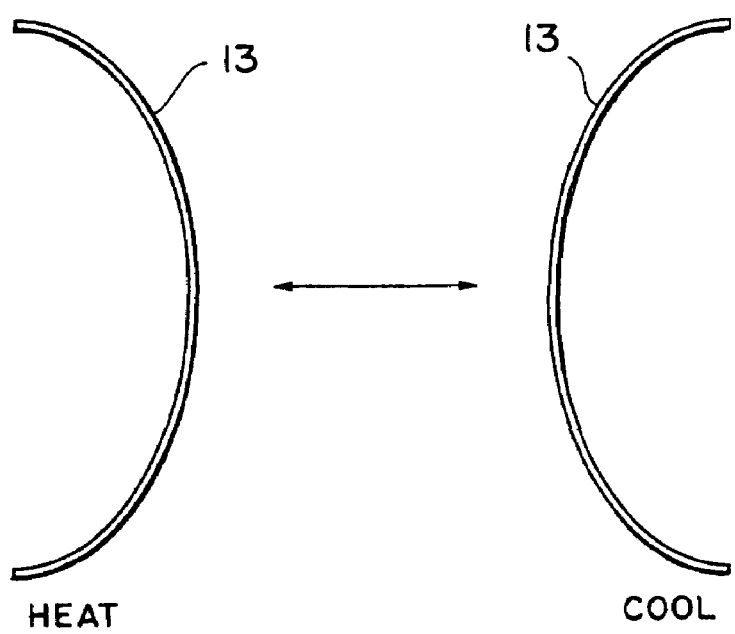
FIG. 2 is a schematic drawing showing shape changing of a shape memory plate used in the artificial sphincter of FIG. 1.

As shown in FIG. 2, when heated and cooled, the shape memory plates 13 change reversibly between two opposite shapes. Specifically, in FIG. 2, a shape memory plate 13 changes between two arc shapes that bend in opposite directions.

Figure 3:
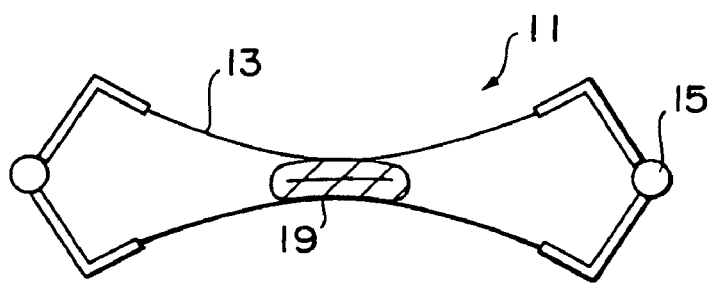
FIG. 3 is a drawing showing a state in which the artificial sphincter of FIG. 1 is constricting the intestine.
Figure 4:
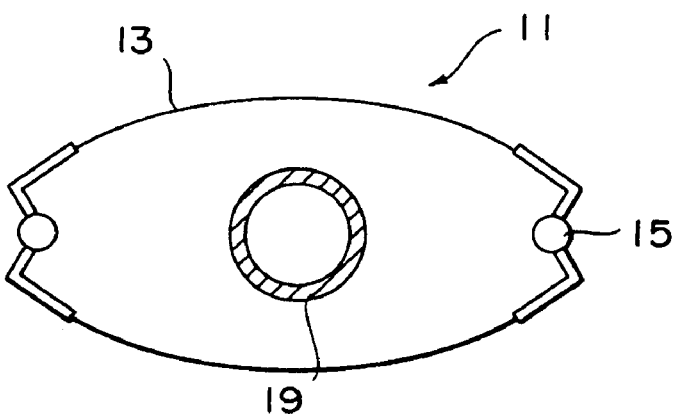
FIG. 4 is a drawing showing a state in which the artificial sphincter of FIG. 1 is not constricting the intestine.

Following is a description of the operation of the artificial sphincter with reference to FIGS. 3 and 4.

FIG. 3 shows the normal state, in which the 2-way shape memory plates 13 are each bent in the opposite direction to the direction of the restraining that was carried out during the aging heat treatment. The intestine 19 is thus constricted by the opening/closing portion 11.

FIG. 4, on the other hand, shows the state during defecation. The 2-way shape memory plates 13 have each been heated and have returned to being bent in the direction of the restraining that was carried out during the aging heat treatment, and hence the constricting force on the intestine 19 has been lost. Here, the heating method was to pass an electric current, but heating through electromagnetic induction, warm water, a current of warm air or the like is also possible.

As described above, with the artificial sphincter according to the first embodiment of the present invention, two shape memory plates 13 are linked together with hinges 15, and as a result the quantity of deformation of the 2-way shape memory plates 13 can be reduced, and moreover a quantity of shape change can be achieved such that the opening opens to a diameter (25 mm) sufficient for unimpeded defecation.

Moreover, the two shape memory plates 13 in the first embodiment of the present invention can be easily separated, and hence there is no need to sever the intestine during installation.

Here, the shape memory alloy used for the 2-way shape memory plates is not limited to being a Ti—Ni alloy, but may also be a Ti—Ni—X alloy (X=Cr, V, Cu, Fe, Co or the like) in which a third element is added, or any of various other kinds such as a Cu shape memory alloy or an Fe shape memory alloy.

Next, a description will be given of an example of application of the artificial sphincter according to the first embodiment of the present invention.

Figure 5:
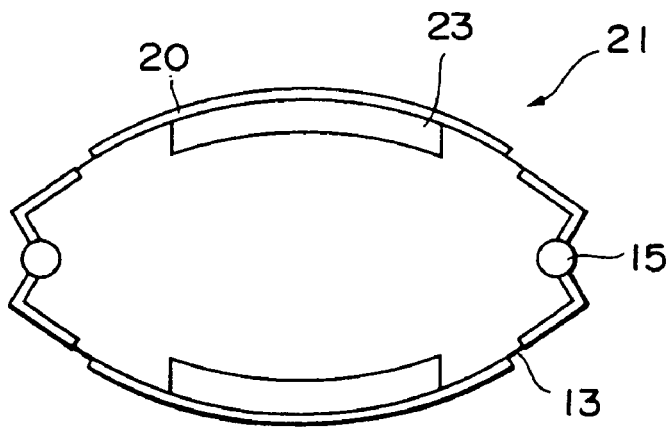
FIG. 5 is a schematic drawing showing an example of application of the artificial sphincter of FIG. 1 to a live animal experiment.

As shown in FIG. 5, sponge rubber 23 is provided in the regions where the artificial sphincter 21 comes into contact with the intestine. This sponge rubber 23 acts as heat insulation and cushioning.

As heating means, formal wires 20 (diameter 0.2 mm) are laid over the shape memory plates 13. These formal wires 20 heat by means of Joule heat.

A live animal experiment was carried out using a sheep, with the artificial sphincter being attached to the small intestine, which is considered to be about the same size as the colon of a human. Firstly, hydrostatic pressure was applied using an injector while at low temperature to produce a state the same as when the actual abdominal pressure is applied, and the ability of the artificial sphincter 21 to close the intestine was evaluated. As a result, it was verified that the intestine is completely closed even at a pressure of 50 mmHg (6.65 kPa), which is greater than 20 mmHg (2.66 kPa), the envisaged abdominal pressure of a human.

Next, with the hydrostatic pressure acting as a load, a direct current was passed through the heaters to heat the shape memory plates, and it was verified whether the artificial sphincter operated to open the intestine and whether internal fluids flowed out. As a result, it was found that internal fluids did indeed flow out with no problem due to the opening operation. It was also found that, after the current was stopped and natural cooling was allowed to occur, the valve closed completely, and thus that there is no problem with the opening/closing operation.

As described above, according to the first embodiment of the present invention, an artificial sphincter that opens and closes, as required, either the anus of a living body or part of the intestine led outside the body can be obtained, wherein this artificial sphincter comprises shape memory alloy elements that change reversibly between two opposite shapes upon changes in temperature and hinges that link these shape memory alloy elements together in a cylindrical shape.

The artificial sphincter according to the first embodiment of the present invention comprises two shape memory alloy elements linked together with hinges, and hence the quantity of deformation of the shape memory alloy elements can be reduced, and moreover a quantity of shape change can be achieved such that the opening opens to a diameter sufficient for unimpeded defecation.

(Second Embodiment)

Figure 6:
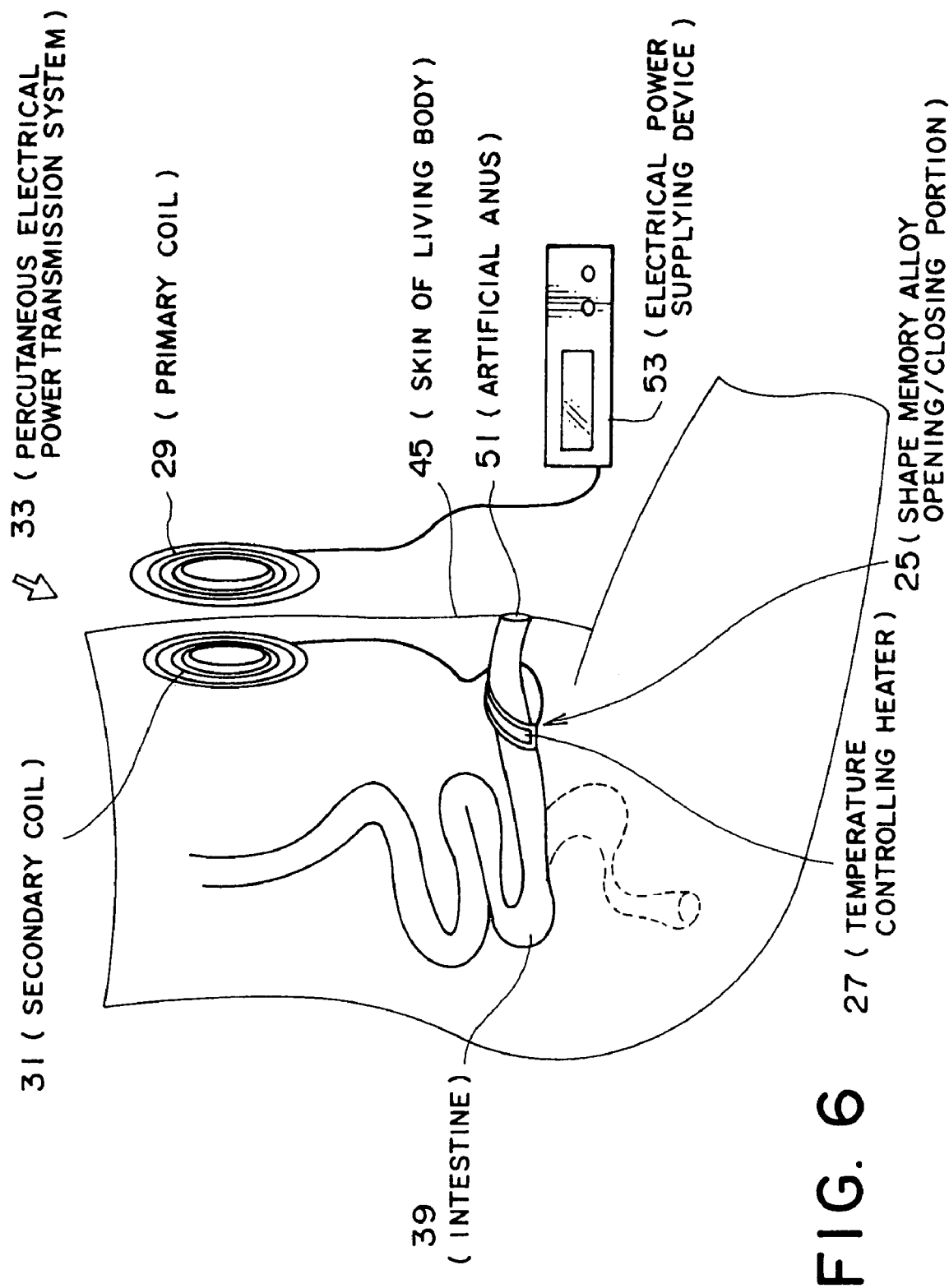
FIG. 6 is an explanatory drawing showing an artificial sphincter according to a second embodiment of the present invention.

Referring to FIG. 6, an artificial sphincter according to a second embodiment of the present invention comprises a shape memory alloy opening/closing portion 25 and temperature controlling heaters 27, wherein electrical power is supplied to the temperature controlling heaters 27 by a percutaneous electrical power transmission system 33 having a coil on the side connected to the power source 53 as a primary coil 29 and a coil on the side connected to the load as a secondary coil 31. In this embodiment, the electrical power is supplied without using a lead wire.

Figure 7:
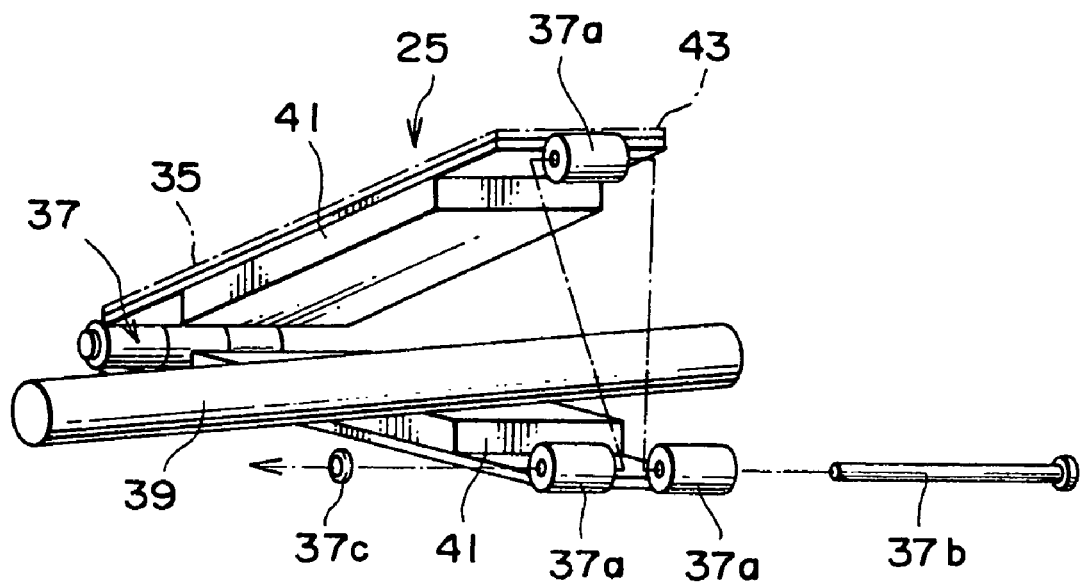
FIG. 7 is a perspective view of the shape memory alloy opening/closing portion of the artificial sphincter of FIG. 6.
Figure 8:
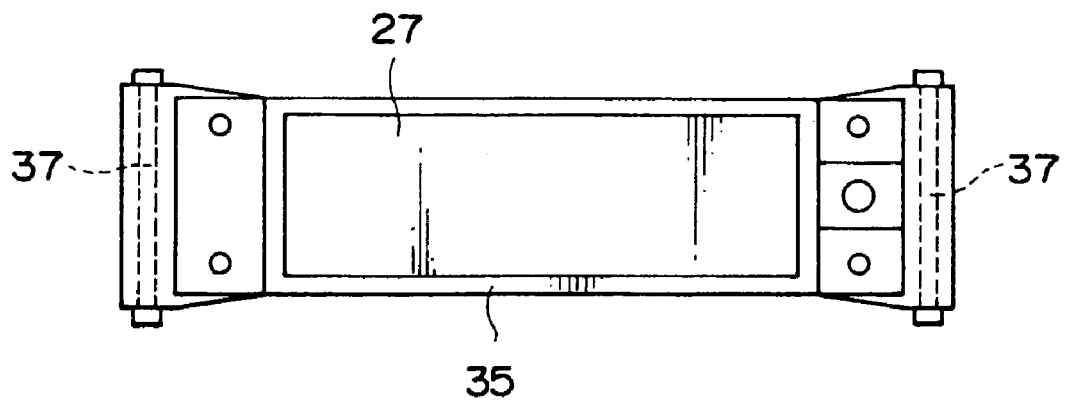
FIG. 8 is a plan view of the shape memory alloy opening/closing portion of the artificial sphincter of FIG. 6.
Figure 9:
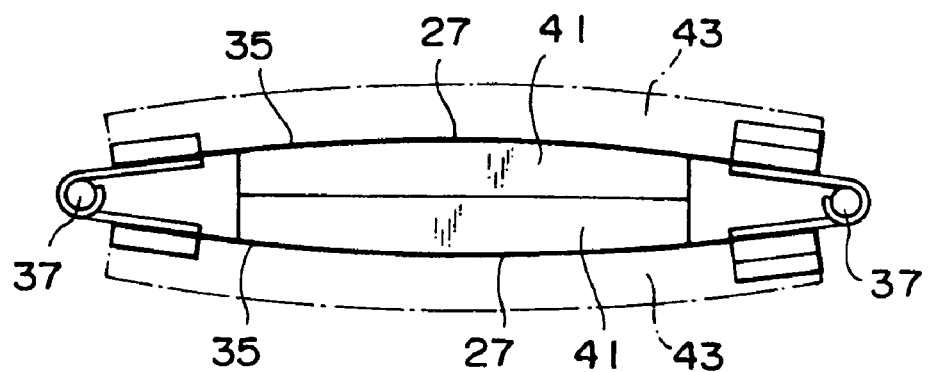
FIG. 9 is a side view of the shape memory alloy opening/closing portion of the artificial sphincter of FIG. 6.

Starting with a description of the shape memory alloy opening/closing portion 25, as shown in FIGS. 7 to 9, this opening/closing portion 25 comprises two shape memory alloy plates 35 as a pair of shape memory alloy elements that each change reversibly between two opposite shapes upon changes in temperature, and cylindrical hinges 37 that link together the end parts (at both ends) of these shape memory alloy plates 35 in such a way as to allow free rotation.

The shape memory alloy plates 35 are, for example, Ti—Ni alloy plates (Ni content 50.4 at %) that have been given a 2-way shape memory property and are generally of thickness 0.5 to 2.0 mm, length 10 to 120 mm and width 5 to 30 mm.

Here, the shape memory alloy used for the 2-way shape memory plates is not limited to being a Ti—Ni alloy, but may also be, for example, a Ti—Ni—X alloy (X=Cr, V, Cu, Fe, Co or the like) in which a third element is added to a Ti—Ni alloy, or any of various other kinds such as a Cu shape memory alloy or an Fe shape memory alloy.

In one example, the shape memory alloy plates 35 are Ti—Ni alloy plates (Ni content 51 at %) of width 18.5 mm, length 70 mm and thickness 0.5 mm.

To give these plates a 2-way shape memory property, solution heat treatment was carried out at 700° C. for 30 minutes, and then, with the plates restrained at a curvature of R40 mm, aging heat treatment was carried out at 400° C. for 100 hours. If heated to 40° C., the plates return to the shape at the time of the aging heat treatment at 400° C. for 100 hours. If cooled to body temperature, the plates change shape, bending backwards in the opposite direction.

Two 2-way shape memory alloy plates 35 obtained in this way were prepared, and were linked in a cylindrical shape near to the intestinal opening using parts of the hinges 37 in such a way that the inside of each of the 2-way shape memory alloy plates 35 was in the direction of restraining at the time of the aging heat treatment, thus forming the opening/closing portion 25 as an artificial sphincter.

The temperature controlling heaters 27 were stuck to the outsides of the shape memory alloy plates 35, and a double layer of medical felt (Bard PTFE felt made by Medicon) was stuck to the surface of each of the temperature controlling heaters 27 so as to thermally insulate the body tissue from the artificial sphincter and obtain biocompatibility.

Moreover, sponge rubber 41, which acts as heat insulation and cushioning, was placed on the inside of the portions that come into contact with the intestine 39, which is the alimentary canal. A medical silicone (Silastic MDX4-4210 made by Toray-Dow Silicone Asia) was applied onto surfaces of the sponge rubber 41 to improve biocompatibility and heat insulation properties.

The shape memory alloy plates 35 can also be covered with a heat-insulating material 43 having good biocompatibility and high heat insulation performance so that there are no adverse effects on the surrounding body tissue. Examples of this heat-insulating material 43 include cork, felt, a polyurethane, a silicone film, or an MPC polymer film.

The hinges 37 each comprise rotating cylinders 37a, a pin 37b and a retaining ring 37c. A material that does not deform much on heating and has good biocompatibility, such as a polycarbonate or hydroxyapatite can be used in the hinges 37. Moreover, metal hinges for which the surfaces are coated with titanium, hydroxyapatite or the like to improve biocompatibility may also be used.

A percutaneous electrical power transmission system 33 is used as the power supply for the temperature controlling heaters 27. Regarding the primary coil 29 connected to the power source and the secondary coil 31 connected to the load (i.e. on the side of the temperature controlling heaters 27), the windings have a structure in which Litz wire comprising a plurality of copper wires of diameter 0.1 mm twisted into a bundle is wound into a flat spiral shape.

Moreover, in addition to this flat spirally wound structure, the primary coil 29 and the secondary coil 31 each have a magnetic body mounted on the surface of the flat spirally wound coil on only one side, wherein this magnetic body has a structure in which Co zero magnetostrictive amorphous magnetic wires of diameter about a few tens of $\mu$m are arranged radially.

The primary coil 29 and the secondary coil 31 are positioned such that the magnetic wires mounted on one side of each of the coils sandwiches the windings of the coils, and electrical power is transmitted non-contactingly by means of electromagnetic induction between the two coils.

During the percutaneous electrical power transmission, the primary coil 29 is positioned on top of the skin 45 of the living body and the secondary coil 31 below the skin 45 in an approximately parallel coaxial position, and electrical power is supplied into the body from the outside without using a lead wire, i.e., in a cordless fashion.

Note that the artificial sphincter may be used to open and close the urethra instead of the intestine 39, in which case the shape of and aging treatment conditions for the shape memory alloy plates 35 and the shape of the hinges 37 may be changed appropriately.

Moreover, one can also envisage permanently installing the primary coil 29 in advance in, for example, a building, such as a toilet. The location of such a toilet can be chosen to be somewhere often used by a patient having the artificial sphincter of the present invention embedded within his/her body, for example the patient's home or company, a hospital or a school. By permanently installing the primary coil 29 in this way, the nuisance of having to carry the primary coil 29 around is eliminated, and even when a patient has lost his/her primary coil 29 and a replacement can not be obtained immediately, measures can be taken easily.

The primary coil 29 and the power source 53 may be formed into a single integral body so as to be conveniently carried by the patient.

Furthermore, as another embodiment, it is also possible for both the primary coil 29 and the secondary coil 31 to be embedded in the living body. In this case, a battery is suitable as the power source connected to the primary coil 29, and even if the secondary coil 31 and the shape memory alloy opening/closing portion 25 are installed in part of the body for which a general anesthetic is necessary, the primary coil 29 can be embedded in part of the body such that replacement is possible under only a local anesthetic.

Following is a description of results of experiments carried out to test the effects of the present invention.

EXAMPLE 1

(i) Transmission coils having amorphous magnetic wires mounted thereon were prepared as the percutaneous electrical power transmission system. Litz wire comprising bundles of 0.1 mm-diameter copper wire was used for the windings. The coils were made to be donut-shaped, which is a shape that gives excellent heat dissipation, and three thousand Co zero magnetostrictive amorphous magnetic wires of expansion diameter 20 $\mu$m were mounted radially on each coil. The magnetic wires were mounted on one side only of each coil, the coils were arranged such that the surfaces on which magnetic wires were not mounted were facing one another, and electrical power was transmitted.

(ii) A rabbit (male; body weight 3 kg) was anesthetized, and the secondary coil of the percutaneous electrical power transmission system was embedded below the skin on the right side of the chest.

EXAMPLE 2

(i) An embedded-within-body type artificial sphincter was prepared by placing two shape memory alloy plates on top of one another and joining together the ends thereof at both ends. The shape memory alloy plates were Ti—Ni alloy plates (Ni content 51 at %) that had been subjected to heat treatment at 850° C. for 10 minutes, then restrained in an arc shape of diameter 50 mm and subjected to aging treatment at 400° C. for 100 hours; these plates exhibited shape memory effects in all directions; the dimensions were width 18.5 mm, length 70 mm and thickness 0.5 mm. The alimentary canal was to be inserted between the two shape memory alloy plates. Sponge rubber, which acts as heat insulation and cushioning, was placed on the portions where the shape memory alloy plates would come into contact with the alimentary canal. A medical silicone (Silastic MDX4-4210 made by Toray-Dow Silicone Asia) was applied onto the surfaces of the sponge rubber.

(ii) Heaters for heating were stuck to the outsides of the shape memory alloy plates, and a double layer of medical felt (Bard PTFE felt made by Medicon) was stuck to the surface of each of the heaters so as to thermally insulate the body tissue from the artificial sphincter and obtain biocompatibility.

Figure 10:
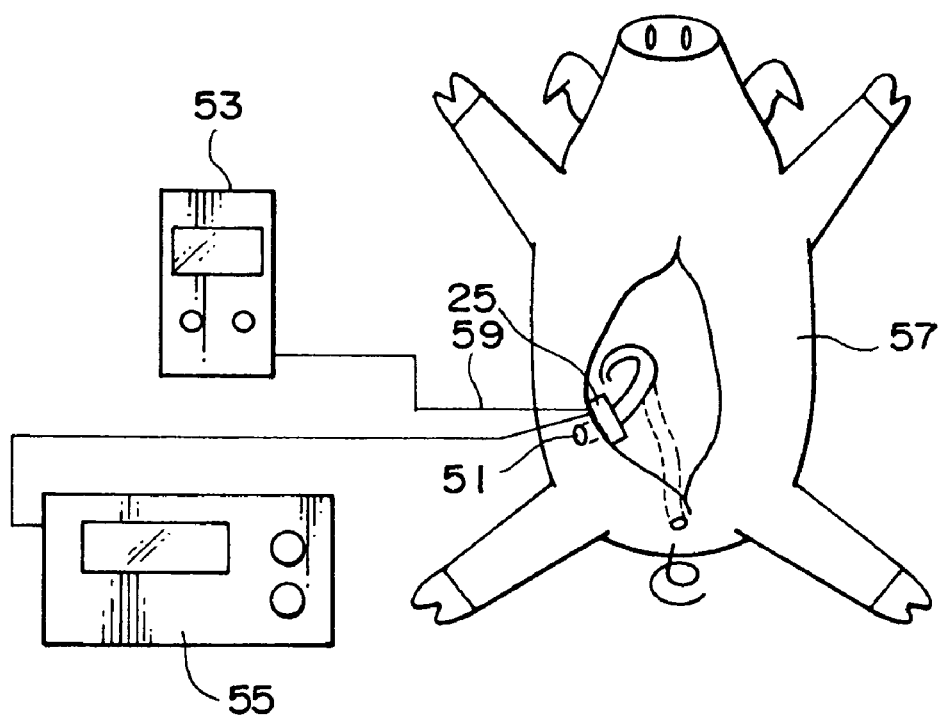
FIG. 10 is an explanatory drawing showing a live animal experiment using a manufactured artificial sphincter.

(iii) A live animal experiment was carried out using the artificial sphincter so prepared. A piglet 57, for which the structure of the alimentary system is similar to that of a human and the size of the alimentary canal is about the same as that of a human, was used in the experiment. As shown in FIG. 10, the piglet 57 was put under general anesthesia, then the abdomen was cut open, the rectum was severed, and one side of the rectum was led through the peritoneum to the abdominal wall and sewn on to form an artificial anus 51. Reference numeral 55 in FIG. 10 represents a temperature measuring device.

The shape memory alloy opening/closing portion 25, which constitutes the artificial sphincter of the present invention, was installed between the peritoneum and the abdominal wall just below the artificial anus 51. Finally, the cut open part was sewn up completely.

(iv) A current was supplied to the shape memory alloy opening/closing portion 25 that constitutes the artificial sphincter from an electrical power supplying device 53 outside the body via a cord 59. The artificial sphincter was opened 3 times a day by supplying a current to the artificial sphincter, thus carrying out defecation from the artificial anus 51.

(v) For 2 weeks after the installation of the artificial sphincter, the piglet showed normal feeding and defecation.

(vi) After 2 weeks, the piglet was dissected and observations made. A considerable amount of pus was found along the cord 59 used for supplying the electrical current to the artificial sphincter. It is thought that an infection got in from outside the body along the cord 59.

The cord 59 becomes unnecessary by providing the percutaneous electrical power transmission system 33 so that the artificial sphincter can be completely embedded into the living body. It is therefore possible to prevent any infection through the cord 59.

As described above, with the artificial sphincter according to the second embodiment of the present invention, an artificial anus can be used without the risk of infection that is present if a tube or stimulating electrode is passed through the skin, and moreover in a psychologically favorable way.

Moreover, according to the second embodiment of the present invention, at low temperature the opening/closing portion is closed and the intestine or the like is blocked off, but when electrical power is supplied to the opening/closing portion by means of a percutaneous electrical power-transmission system, the opening/closing portion is heated and opens, and defecation occurs from the artificial anus.

In this way, according to the present invention, in addition to the above-mentioned effects, because the shape memory alloy opening/closing portion comprises two shape memory alloy plates linked together at both ends with hinges, there is no mechanism for a bias spring, which is indispensable in conventional SMA actuators, and hence the artificial sphincter has a simple structure.

Moreover, according to the present invention, with regard to the places in which the artificial sphincter can be used, the artificial sphincter can, for example, open and close, as required, the anus of a living body or part of the intestine led outside the body, or open and close, as required, part of the urethra in a living body.

Moreover, according to the present invention, by additionally providing heat-insulating cushioning members on the inside and/or the outside, the living body can be insulated from heat and cushioned, and moreover, according to the present invention, by covering the artificial sphincter with a biocompatible material, care can be taken such that there will be no adverse effects on the surrounding body tissue.

Moreover, according to the present invention, the coils have a flat spirally wound structure, and due to this flatness do not take up much space, and according to the present invention as disclosed in claim 8, a strong magnetic force can be obtained by mounting amorphous magnetic wires.

Moreover, according to the present invention, the nuisance of having to carry around a primary coil is eliminated, and situations such as the primary coil being lost and it not being possible to obtain a replacement immediately are avoided.

Moreover, according to the present invention, a battery is suitable as the power source connected to the primary coil, and even if the secondary coil and the shape memory alloy opening/closing portion are installed in part of the body for which a general anesthetic is necessary, the primary coil can be embedded in part of the body such that replacement is possible under only a local anesthetic.

What is claimed is:

1. An artificial sphincter comprising a shape memory alloy opening/closing portion comprising hinges and temperature controlling heaters, wherein electrical power is supplied to said temperature controlling heaters by a percutaneous electrical power transmission system having a coil on a side connected to a power source as a primary coil and a coil on a side connected to a load as a secondary coil.

2. The artificial sphincter according to claim 1, wherein said shape memory alloy opening/closing portion comprises two shape memory alloy plates linked together at both ends by hinges and adapted to be disposed on opposite sides of a lumen in a living body.

3. The artificial sphincter according to claim 2, wherein heat-insulating cushioning members are additionally provided on said two shape memory alloy plates.

4. The artificial sphincter according to claim 2, wherein said two shape memory alloy plates are covered with a biocompatible material.

5. The artificial sphincter according to claim 1, wherein said shape memory alloy opening/closing portion opens and closes, as required, either an anus of a living body or part of an intestine of a living body led outside said body.

6. The artificial sphincter according to claim 1, wherein said shape memory alloy opening/closing portion opens and closes, as required, part of a urethra in a living body.

7. The artificial sphincter according to claim 1, wherein said coils have a flat spirally wound structure.

8. The artificial sphincter according to claim 7, wherein said coils have a flat spirally wound structure having mounted thereon amorphous magnetic wires.

9. The artificial sphincter according to claim 1, wherein said primary coil and a power supply are formed into a single integral body of a portable type.

10. The artificial sphincter according to claim 1, wherein said secondary coil, said temperature controlling heaters, and said shape memory alloy opening/closing portion are adapted to be completely embedded in a living body.

11. The artificial sphincter according to claim 10, wherein said primary coil is adapted to be completely embedded in a living body.

12. The artificial sphincter according to claim 1, wherein said primary coil is permanently installed in advance in a building or the like.

* * * * *